United States Patent
Chen

(10) Patent No.: US 11,307,127 B2
(45) Date of Patent: Apr. 19, 2022

(54) POWER CONSUMPTION DETECTION SYSTEM

(71) Applicant: KAUO JEI IND CO., LTD., New Taipei (TW)

(72) Inventor: Wen-Ho Chen, New Taipei (TW)

(73) Assignee: KAUO JEI IND CO., LTD., New Taipei (TW)

( * ) Notice: Subject to any disclaimer, the term of this patent is extended or adjusted under 35 U.S.C. 154(b) by 102 days.

(21) Appl. No.: 16/568,223

(22) Filed: Sep. 11, 2019

(65) Prior Publication Data

US 2021/0072132 A1 Mar. 11, 2021

(51) Int. Cl.
  *G01N 11/14* (2006.01)
  *G01R 22/06* (2006.01)
  *G01N 33/44* (2006.01)

(52) U.S. Cl.
  CPC ......... *G01N 11/142* (2013.01); *G01N 33/445* (2013.01); *G01R 22/06* (2013.01)

(58) Field of Classification Search
  CPC .. G01N 11/142; G01N 33/445; G01N 11/145; G01R 22/06
  USPC ........... 73/54.01, 54.02, 54.23, 54.28–54.35, 73/54.37, 866
  See application file for complete search history.

(56) References Cited

U.S. PATENT DOCUMENTS

2015/0360399 A1* 12/2015 Grosz .................... B29B 7/007
                                                         264/138

FOREIGN PATENT DOCUMENTS

| CN | 1198130 C   |   | 4/2005 |
|----|-------------|---|--------|
| CN | 207066925 U |   | 3/2018 |
| SU | 1024455     | * | 3/1983 |
| WO | 03006955 A1 |   | 1/2003 |

OTHER PUBLICATIONS

Office Action dated Dec. 13, 2019 of the corresponding Taiwan patent application.

* cited by examiner

*Primary Examiner* — Robert R Raevis
(74) *Attorney, Agent, or Firm* — Chun-Ming Shih; HDLS IPR Services

(57) ABSTRACT

A power consumption detection system includes a controller, a rubber sampling module, a rubber calender, a temperature control module, a mooney sensor, and a power meter. The rubber sampling module samples a rubber material according to a weight value and obtains a rubber to be tested. The rubber calender continuously calenders the rubber to be tested at least six times. The temperature control module maintains the rubber to be tested with a temperature value. The mooney sensor obtains an actual viscosity index and the controller controls the calendaring number of the rubber calender until the target viscosity index is consistent with the actual viscosity index. The power meter records a power consumed by the rubber calender and obtains a power consumption value.

10 Claims, 3 Drawing Sheets

POWER CONSUMPTION DETECTION SYSTEM

BACKGROUND

Technical Field

The present disclosure relates to a power consumption detection system, and more particularly to a power consumption detection system for rubber processing.

Description of Related Art

The statements in this section merely provide background information related to the present disclosure and do not necessarily constitute prior art.

In the field of rubber testing, such as the national standard of the People's Republic of China (GB), the International Organization for Standardization (ISO), the American Society for Testing and Materials (ASTM), and Rubber Research Institute of Malaysia (RRIM), outside of North America, ISO standards have gradually become popular.

However, in the field of rubber testing, there is still a lack of a one-stop system for rapid and continuous detection of rubber. Moreover, when rubber is actually produced and applied to a commercial production line, since a roller pitch of a rubber calender and a temperature of a rubber to be tested cannot be accurately controlled according to the rubber to be tested having a specific sampling weight, accurate electric power consumption values cannot be obtained. This has caused problems for rubber testing companies and rubber-related manufacturers, and increased production costs.

Therefore, how to design a power consumption detection system to solve the technical problems above is an important subject studied by the inventors and proposed in the present disclosure.

SUMMARY

The purpose of the present disclosure is to provide a power consumption detection system, which can accurately control a roller pitch of a rubber calender and a temperature value of a rubber to be tested according to the rubber to be tested having a specific sampling weight, thereby obtaining an accurate power consumption value. And to achieve the purpose of reducing the production costs of rubber-related manufacturing.

In order to achieve the purpose above-mentioned, the power consumption detection system applied to a rubber raw material comprising a controller, a rubber sampling module, a rubber calender, a temperature control module, a mooney sensor and a power meter. The controller that produces a weight value, a temperature value, a target mooney index, and a roller pitch. The rubber sampling module is coupled to the controller, and the rubber sampling module samples the rubber raw material according to the weight value to obtain a rubber to be tested comply with the weight value. The rubber calender coupled to the controller and the rubber sampling module, the rubber calender including two rollers arranged in parallel, the two rollers are spaced apart from each other by the roller pitch and continuously calendering the rubber to be tested at least six times. The temperature control module coupled to the controller and the rubber calender, the temperature control module maintaining the rubber to be tested to have a temperature value. The mooney sensor coupled to the controller, the temperature control module, and the rubber calender, when the temperature control module determines that the rubber to be tested in the rubber calender has reached the temperature value, the mooney sensor obtains an actual mooney index from the rubber to be tested in the rubber calender, and the controller controls the two rollers has a number of rolling times to calender the rubber to be tested according to the target mooney index and the actual mooney index, until the target mooney index is consistent with the actual mooney index. The power meter coupled to the controller, the mooney sensor, and the rubber calender, when the mooney sensor determines that the target mooney index consistent with the actual mooney index, the power meter records and obtains a power consumption value from the rubber calender.

In one embodiment, the weight value is 360 grams.

In one embodiment, the temperature value is 25 degrees Celsius.

In one embodiment, the target mooney index has a mooney viscosity between 61.07 and 91.06.

In one embodiment, the roller pitch is 1.65 mm.

In one embodiment, the two rollers include a front roller and a rear roller, wherein the front roller rotates between 21 rpm and 24 rpm, and the rear roller rotates at 31 rpm.

In one embodiment, the speed ratio of the two rollers is 1:1.4.

In one embodiment, the power meter obtains the power consumption value by subtracting a power of the previous record from a power of the current record of the rubber calender.

In one embodiment, the temperature control module is a water-cooled chiller.

In one embodiment, the power consumption detection system further comprising a cloud server, the cloud server coupled to the power meter and stores the power consumption value.

When operating the power consumption detection system, the controller causes the rubber sampling module to obtain the rubber to be tested according to the weight value. Then the controller causes the two rollers of the rubber calender are spaced apart from each other by the roller pitch and continuously calendering the rubber to be tested at least six times at the same time, the controller causes the temperature control module maintaining the rubber to be tested to have the temperature value. When the temperature control module determines that the rubber to be tested in the rubber calender has reached the temperature value, the mooney sensor obtains an actual mooney index from the rubber to be tested in the rubber calender, and the controller controls the two rollers has a number of rolling times to calender the rubber to be tested according to the target mooney index and the actual mooney index, until the target mooney index is consistent with the actual mooney index. At this time, the power meter records and obtains the power consumption value from the rubber calender. To this end, according to the rubber to be tested has the weight value as a specific sampling weight, the present disclosure can accurately control the roller pitch of the rubber calender and the temperature value of the rubber to be tested, thereby obtaining an accurate power consumption value and achieving the purpose to reduce the production cost of the rubber-related manufacturing industry.

In order to further understand the techniques, means, and effects of the present disclosure for achieving the intended purpose. Please refer to the following detailed description and drawings of the present disclosure. The drawings are provided for reference and description only, and are not intended to limit the present disclosure.

DETAILED DESCRIPTION

Figure 1:
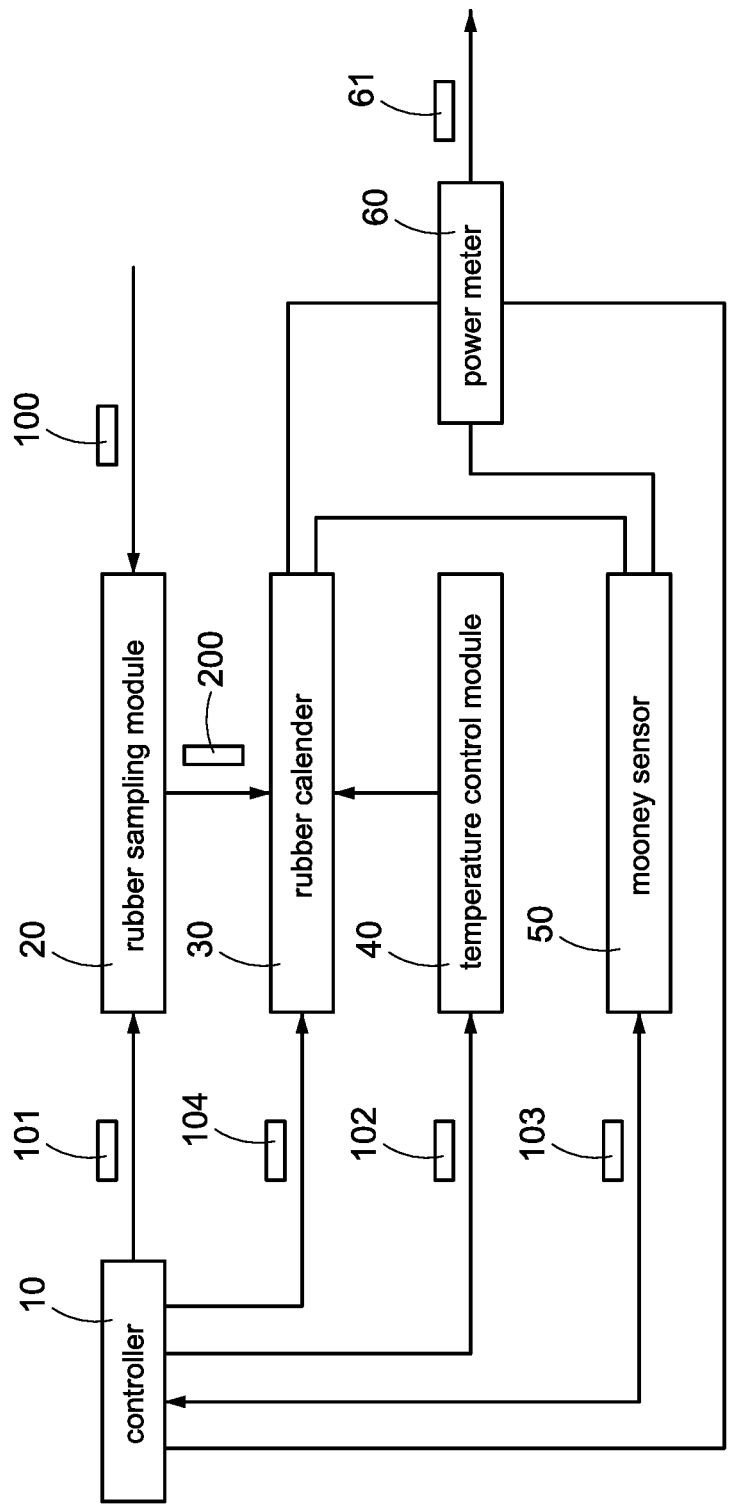
FIG. 1 is an architectural diagram of a first embodiment of a power consumption detection system of the present disclosure.

The embodiments of the present disclosure are described by way of specific examples, and those skilled in the art can readily appreciate the other advantages and functions of the present disclosure. The present disclosure may be embodied or applied in various other specific embodiments, and various modifications and changes can be made without departing from the spirit and scope of the present disclosure.

It should be understood that the structures, the proportions, the sizes, the number of components, and the like in the drawings are only used to cope with the contents disclosed in the specification for understanding and reading by those skilled in the art, and it is not intended to limit the conditions that can be implemented in the present disclosure, and thus is not technically significant. Any modification of the structure, the change of the proportional relationship, or the adjustment of the size, should be within the scope of the technical contents disclosed by the present disclosure without affecting the effects and the achievable effects of the present disclosure.

The technical content and detailed description of the present disclosure will be described below in conjunction with the drawings.

Figure 2:
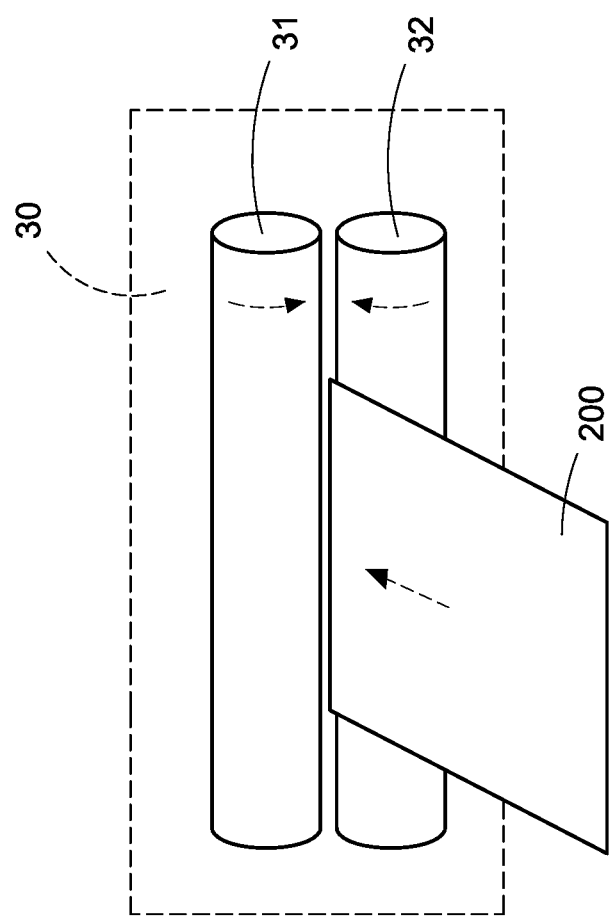
FIG. 2 is a schematic view of a rubber calender according to the first embodiment of the power consumption detection system of the present disclosure.

Please refer to FIG. 1 and FIG. 2. FIG. 1 is an architectural diagram of a first embodiment of a power consumption detection system of the present disclosure. FIG. 2 is a schematic view of a rubber calender according to the first embodiment of the power consumption detection system of the present disclosure.

The power consumption detection system of the present disclosure is applied to a rubber raw material 100, including a controller 10, a rubber sampling module 20, a rubber calender 30, a temperature control module 40, a mooney sensor 50, and a power meter 60. The controller 10 produces a weight value 101, a temperature value 102, a target mooney index 103, and a roller pitch 104. The controller 10 may be one of a CPU, an MPU, an ASIC, and a SoC.

The rubber sampling module 20 is coupled to the controller 10, and the rubber sampling module 20 samples the rubber raw material 100 according to the weight value 101 to obtain a rubber to be tested 200 in accordance with the weight value 101. The rubber sampling module 20 may be a device consisting of a robot arm, a cutter, and a conveyor belt. In the first embodiment of the present disclosure, the weight value 101 is 360 grams.

The rubber calender 30 is coupled to the controller 10 and the rubber sampling module 20, and the rubber calender 30 includes two rollers arranged in parallel. The two rollers include a front roller 31 and a rear roller 32, and the two rollers are spaced apart from each other by the roller pitch 104 and continuously calendering the rubber to be tested 200 at least six times. As shown in FIG. 2, the front roller 31 and the rear roller 32 rotate in opposite directions to each other, and the rubber to be tested 200 is rolled into the rubber calender 30. The front roller 31 rotates between 21 rpm and 24 rpm, and the rear roller 32 rotates at 31 rpm. In the first embodiment of the present disclosure, the roller pitch 104 is 1.65 mm, and the optimum speed ratio of the front roller 31 to the rear roller 32 is 1:1.4.

The temperature control module 40 is coupled to the controller 10 and the rubber calender 30, and the temperature control module 40 maintains the rubber to be tested 200 to have a temperature value 102. In a first embodiment of the present disclosure, the temperature value 102 is 25 degrees Celsius. In the first embodiment of the present disclosure, the temperature control module 40 is a water-cooled chiller.

The mooney sensor 50 is coupled to the controller 10, the temperature control module 40, and the rubber calender 30. When the temperature control module 40 determines that the rubber to be tested 200 in the rubber calender 30 has reached the temperature value 102, the mooney sensor 50 obtains an actual mooney index (not shown) from the rubber to be tested 200 in the rubber calender 30. The controller 10 controls the two rollers (i.e., the front roller 31 and the rear roller 32) having a number of rolling times to calender the rubber to be tested 200 according to the target mooney index 103 and the actual mooney index, until the target mooney index 103 is consistent with the actual mooney index. In a first embodiment of the present disclosure, the target mooney index 103 has a mooney viscosity between 61.07 and 91.06. The mooney viscosity is a comprehensive index of hardness, viscosity, and flow rate of natural rubber. The higher value of the mooney viscosity means harder, less sticky, poor fluidity and low plasticity. On the contrary, the lower value of the mooney viscosity means softer, more sticky, better fluidity and higher plasticity.

The power meter 60 is coupled to the controller 10, the mooney sensor 50, and the rubber calender 30. When the mooney sensor 50 determines that the target mooney index 103 consistent with the actual mooney index, the power meter 60 records and obtains a power consumption value 61 from the rubber calender 30. In the first embodiment of the present disclosure, the power meter 60 subtracts the power recorded by the rubber calender 30 from the previous recorded power to obtain the power consumption value 61. That is to say, the power meter 60 can know the difference between different test procedures according to the continuous or discontinuous multiple test procedures. By comparing different rubber grades or different rubber types used in each test, rubber testers and rubber-related manufacturers can easily control power consumption and cost.

For example, the power meter 60 records a power consumption value from the rubber calender 30 for 360 grams of the rubber to be tested from the mooney viscosity is 91 (i.e., the actual mooney index) to reduce to the target mooney index 103 (mooney viscosity between 61.07 and 91.06). The power consumption value the is 1.3652 kW. The power meter 60 records a power consumption value from the rubber calender 30 for 360 grams of the rubber to be tested from the mooney viscosity is 78.18 (i.e., the actual mooney index) to reduce to the target mooney index 103. The power consumption value the is 0.852 kW. For this reason, it can be known that the power consumption value of the rubber calender 30 for the rubber to be tested A to consist with the target mooney index 103 is 1.3652 kW. The power consumption value of the rubber calender 30 for the rubber to be tested B to consist with the target mooney index 103 is 0.852 kW. It can be further learned that 360 gram of the rubber to be tested A consumes 0.5132 kW more than 360 gram of the rubber to be tested B in the actual commercial process, that is, the rubber to be tested A consumes 1.43 Watts more per gram than the rubber to be tested B.

Further, since the rubber trading market is trading and processing in a relatively large order of magnitude, it is important to accurately estimate the production cost of the rubber-related industry (such as the tire industry, medical rubber or daily necessities, etc.) for the power consumption value 61.

Figure 3:
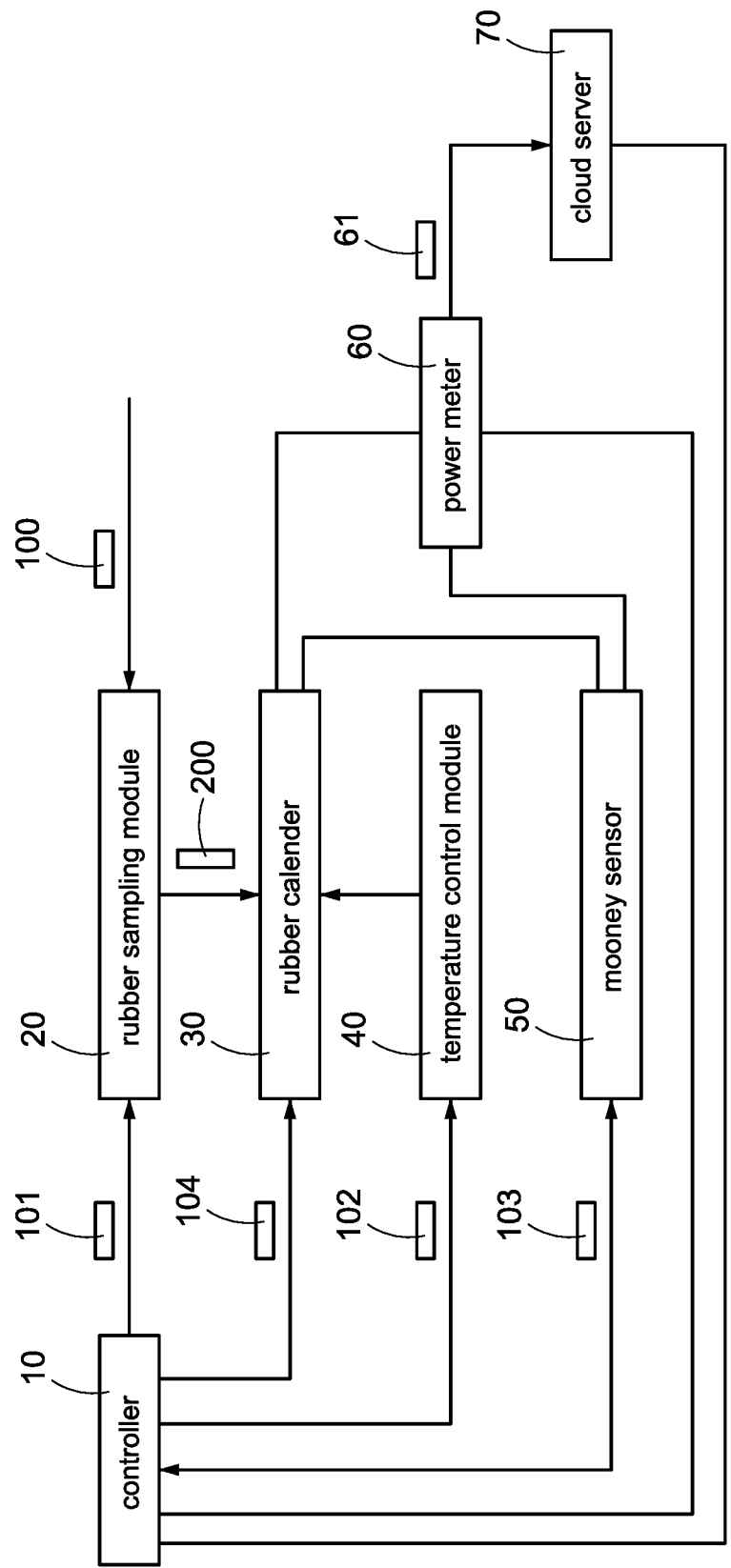
FIG. 3 is an architectural diagram of a second embodiment of the power consumption detection system of the present disclosure.

Please refer to FIG. 3, which is a structural diagram of a second embodiment of the power consumption detection system of the present disclosure. The first embodiment of the present disclosure is substantially the same as the second embodiment, but the second embodiment further includes a cloud server 70. The cloud server 70 is coupled to the power meter 60 and the controller 10 and stores the power consumption value 61. The cloud server 70 is used for access by users, administrators, or operators, and can control access rights of the power consumption value 61 in combination with RFID, fingerprint, voiceprint, face recognition, and the like. However, the present disclosure is not limited thereto.

When operating the power consumption detection system, the controller 10 causes the rubber sampling module 20 to obtain the rubber to be tested 200 according to the weight value 101. Then the controller 10 causes the two rollers (the front roller 31 and the rear roller 32) of the rubber calender 30 are spaced apart from each other by the roller pitch 104 and continuously calendering the rubber to be tested 200 at least six times at the same time, the controller 10 causes the temperature control module 40 maintaining the rubber to be tested 200 to have the temperature value 102. When the temperature control module 40 determines that the rubber to be tested 200 in the rubber calender 30 has reached the temperature value 102, the mooney sensor 50 obtains an actual mooney index from the rubber to be tested 200 in the rubber calender 30, and the controller 10 controls the two rollers (the front roller 31 and the rear roller 32) has a number of rolling times to calender the rubber to be tested 200 according to the target mooney index 103 and the actual mooney index, until the target mooney index 103 is consistent with the actual mooney index. At this time, the power meter 60 records and obtains the power consumption value 61 from the rubber calender 30. To this end, according to the rubber to be tested 200 has the weight value 101 as a specific sampling weight, the present disclosure can accurately control the roller pitch 104 of the rubber calender 30 and the temperature value 102 of the rubber to be tested 200. Further, the difference between the different test procedures can be known according to the continuous or discontinuous multiple test procedures, and the different rubber grades or different rubber types used for each test can be compared. Thereby obtaining an accurate power consumption value 61 and achieving the purpose to reduce the production cost of the rubber-related manufacturing industry.

The rubber industry knows that the closer to the equator, the higher the average natural rubber production capacity, the better the average quality and the thicker the secreted gum. The above-mentioned technology has accumulated many years of experience and research and development design, and can be a calculation model and testing equipment for natural rubber, which can test and calculate the loss of specific gravity, loss of rubber expansion rate, loss of power consumption, manpower and machine wear. It is possible to calculate the misunderstanding of the price and value of the natural rubber of various grades and numbers, and can analyze the comparative data of the price and value of the natural rubber. From then on, it can be avoided to the greatest extent that the label of the natural rubber is incorrect, or because the lack of correct data, the procurement personnel only purchase according to their rules of thumb or market conditions, or human error, resulting in invisible losses. Especially for companies with a large amount of natural rubber, the use of the aforementioned technology will certainly reduce the cost of raw material procurement, or increase the production cost due to non-optimal specifications, and also avoid the mistakes of the procurement staff or the opaque zone. It saves a lot of money and avoids the waste of global resources for the human, tire and natural rubber industries.

The above is only a detailed description and drawings of the preferred embodiments of the present disclosure, but the features of the present disclosure are not limited thereto, and are not intended to limit the present disclosure. All the scope of the present disclosure shall be subject to the scope of the following claims. The embodiments of the spirit of the present disclosure and its similar variations are intended to be included in the scope of the present disclosure. Any variation or modification that can be easily conceived by those skilled in the art in the field of the present disclosure can be covered by the following claims.

What is claimed is:

1. A power consumption detection system applied to a rubber raw material, comprising:
    a controller configured to provide a weight value, a temperature value, a target mooney index, and a roller pitch,
    a rubber sampling module coupled to the controller, and the rubber sampling module configured to obtain a rubber to be tested comply with the weight value,
    a rubber calender coupled to the controller and the rubber sampling module, the rubber calender including two rollers arranged in parallel, the two rollers spaced apart from each other by the roller pitch and continuously calendering the rubber to be tested at least six times,
    a temperature control module coupled to the controller and the rubber calender, the temperature control module configured to maintain the rubber to be tested to have a temperature value,
    a mooney sensor coupled to the controller, the temperature control module, and the rubber calender, when the temperature control module determining that the rubber to be tested in the rubber calender has reached the temperature value, the mooney sensor configured to obtain an actual mooney index from the rubber to be tested in the rubber calender, and the controller configured to control the two rollers has a number of rolling times to calender the rubber to be tested according to the target mooney index and the actual mooney index, until the target mooney index being consistent with the actual mooney index, and
    a power meter coupled to the controller, the mooney sensor, and the rubber calender, when the mooney sensor determines that the target mooney index is consistent with the actual mooney index, the power meter is configured to record and obtain a power consumption value from the rubber calender.

2. The power consumption detection system in claim 1, wherein the weight value is 360 grams.

3. The power consumption detection system in claim 1, wherein the temperature value is 25 degrees Celsius.

4. The power consumption detection system in claim 1, wherein the target mooney index has a mooney viscosity between 61.07 and 91.06.

5. The power consumption detection system in claim 1, wherein the roller pitch is 1.65 mm.

6. The power consumption detection system in claim 1, wherein the two rollers include a front roller and a rear roller, wherein the front roller rotates between 21 rpm and 24 rpm, and the rear roller rotates at 31 rpm.

7. The power consumption detection system in claim 1, wherein the speed ratio of the two rollers is 1:1.4.

8. The power consumption detection system in claim 1, wherein the power meter obtains the power consumption value by subtracting a power of the previous record from a power of the current record of the rubber calender.

9. The power consumption detection system in claim 1, wherein the temperature control module is a water-cooled chiller.

10. The power consumption detection system in claim 1, further comprising a cloud server, the cloud server coupled to the power meter and configured to store the power consumption value.

\* \* \* \* \*